(12) United States Patent
Leak et al.

(10) Patent No.: US 12,733,915 B2
(45) Date of Patent: Sep. 15, 2026

(54) IMAGE GUIDED BIOPSY NEEDLE

(71) Applicant: Veran Medical Technologies, LLC, Golden, CO (US)

(72) Inventors: David M. Leak, Brooklyn Park, MN (US); Kester Julian Batchelor, Mound, MN (US); Eric Stender, Champlin, MN (US)

(73) Assignee: Veran Medical Technologies, LLC, Golden, CO (US)

( * ) Notice: Subject to any disclaimer, the term of this patent is extended or adjusted under 35 U.S.C. 154(b) by 0 days.

(21) Appl. No.: 18/671,176

(22) Filed: May 22, 2024

(65) Prior Publication Data

US 2024/0389985 A1 Nov. 28, 2024

Related U.S. Application Data

(60) Provisional application No. 63/504,243, filed on May 25, 2023.

(51) Int. Cl.

| | |
|---|---|
| ***A61B 10/04*** | (2006.01) |
| ***A61B 8/00*** | (2006.01) |
| ***A61B 8/12*** | (2006.01) |
| ***A61B 17/34*** | (2006.01) |

(52) U.S. Cl.

CPC ................ *A61B 10/04* (2013.01); *A61B 8/12* (2013.01); *A61B 8/445* (2013.01); *A61B 17/3403* (2013.01); *A61B 2010/045* (2013.01); *A61B 2017/3413* (2013.01)

(58) Field of Classification Search

CPC ........... A61B 10/04; A61B 8/12; A61B 8/445; A61B 17/3403; A61B 2010/045; A61B 2017/3413

See application file for complete search history.

(56) References Cited

U.S. PATENT DOCUMENTS

| | | | | |
|---|---|---|---|---|
| 11,992,258 B2 * | 5/2024 | Placek ............... | A61B 18/1477 | |
| 2006/0189972 A1 * | 8/2006 | Grossman .......... | A61B 18/1477 | 606/41 |
| 2012/0197157 A1 * | 8/2012 | Ryan ...................... | A61B 10/04 | 600/567 |
| 2016/0030021 A1 * | 2/2016 | Pasternak ............. | A61B 10/04 | 600/424 |
| 2021/0321994 A1 * | 10/2021 | Fleury ................... | A61B 8/483 | |

(Continued)

*Primary Examiner* — Amal Aly Farag

(74) *Attorney, Agent, or Firm* — Schwegman Lundberg & Woessner, P.A.

(57) ABSTRACT

A medical device having a handle and an elongate member extending from the handle is provided. The elongate member defines an elongate member lumen where a biopsy needle extends through the elongate member lumen. The medical device has an imaging device extending through a biopsy needle lumen of the biopsy needle. The imaging device extends between a proximal end of the biopsy needle and a distal end of the biopsy needle. The medical device has an elongate member opening at a distal end of the elongate member and a biopsy needle deployment feature proximate to the elongate member opening. The biopsy needle deployment feature moves between a first configuration and a second configuration. In the first configuration, the biopsy needle extends past the elongate member opening and in the second configuration the biopsy needle extends through the elongate member opening.

19 Claims, 13 Drawing Sheets

(56) References Cited

U.S. PATENT DOCUMENTS

| | | | | |
|---|---|---|---|---|
| 2022/0133284 | A1* | 5/2022 | Lampotang | A61B 10/0241 600/562 |
| 2022/0313208 | A1* | 10/2022 | True | A61B 8/4416 |
| 2022/0378400 | A1* | 12/2022 | Yu | A61B 8/5215 |

* cited by examiner 104
700
700A
1300
1306
806A
806
804
1304
1302
1308
700A
1300

104
502
402
1400
1402
402
A
1400
Z
W
X
Y

IMAGE GUIDED BIOPSY NEEDLE

PRIORITY CLAIM

This application claims the benefit of priority to U.S. Patent Application Ser. No. 63/504,243, filed May 25, 2023, the contents of which are hereby incorporated by reference.

TECHNICAL FIELD

This document pertains generally, but not by way of limitation, to medical devices that can be used for various medical procedures. More specifically, but not by way of limitation, this document relates to a medical device that can incorporate an imaging device with a biopsy needle.

BACKGROUND

When a practitioner desires to gather a sample at a target site, such as a lung tissue sample, the practitioner maneuvers a medical device to the target site and removes the sample. Typically, the medical device includes a biopsy needle, which is delivered to the target site and used to remove the sample. In lumens not large enough for a camera/scope with a working channel for the biopsy needle, a separate camera is often used for navigation. Once at the target site, the camera is removed, and a biopsy needle is delivered to the target site to acquire and remove the sample.

As the sample is being procured without a camera, there is no way to view the navigation of the biopsy needle to the target being sampled. In addition, viewing a volume of the sample the biopsy needle is removing at the biopsy needle in real-time is not possible.

SUMMARY

In lumens too small for a scope with a camera and working channel, what is needed is a reduced profile medical device that is achieved by incorporating an imaging device within a biopsy needle itself that in turn provides navigation assistance to a target site. The medical device can include an elongate member that defines an elongate member lumen within which the biopsy needle can extend. The biopsy needle can define a lumen within which the imaging device can be disposed. The imaging device can be extendable within the biopsy needle lumen to a distal tip of the biopsy needle. The imaging device can assist with navigating the medical device to a target site within a patient. The imaging device can also be retractable within the biopsy needle lumen to allow for the resection of a sample from a target site with the biopsy needle.

The elongate member can have an elongate member opening located at a distal end of the elongate member. When the medical device is at the target site, the elongate member opening can be adjacent to the target site. Furthermore, a biopsy needle deployment feature can be disposed within the elongate member lumen and proximate the elongate member opening. The biopsy needle deployment feature can be movable between a first configuration and a second configuration.

In the first configuration, the biopsy needle deployment feature can be substantially flat such that the biopsy needle deployment feature does not interfere with the biopsy needle and the imaging device extending and retracting within the elongate member lumen. More specifically, the biopsy needle and the imaging device can pass over the biopsy needle deployment feature and to a distal end of the elongate member without being obstructed by the biopsy needle deployment feature.

In the second configuration, the biopsy needle deployment feature can form a ramp that has a peak extending through the elongate member opening. When the biopsy needle deployment feature is in the second configuration, the biopsy needle can extend through the elongate member lumen, up the ramp, and into the target site. By virtue of being disposed within the biopsy needle, the imaging device can extend into the target site to assist with the navigation of the biopsy needle within the target site and assist with the identification of a sample to be resected from the target site.

Having a biopsy needle with selectable deployment orientation to the elongated member of either on-axis or off-axis enhances can enhance a device's ability to procure a sample for targets located centrically and eccentrically respectively to the elongated member.

Upon identification of the target to sample, the imaging device can be retracted from the distal tip of the biopsy needle. The biopsy needle can then be used to acquire the sample. The biopsy needle can include landmarks at an interior surface. As the sample is withdrawn into the biopsy needle, the imaging device can show the amount of the sample that is being resected using the landmarks.

A potential advantage relates to providing a device having a biopsy needle that incorporates an imaging device thereby avoiding the need to withdraw an imaging device when the device reaches a target site and then providing a separate biopsy needle.

A potential advantage includes the ability to identify a sample to be removed when the biopsy needle is at the target site using the imaging device incorporated into the biopsy needle.

Another potential advantage relates to using the imaging device to prevent coring at the target site as the biopsy needle advances through the target site to resect a sample.

A further potential advantage relates to being able to determine how much of a sample has been resected from a target site using the imaging device and the landmarks.

DETAILED DESCRIPTION

Examples relate to a medical device that incorporates an imaging device within a biopsy needle that can be used to assist with the navigation of the medical device and the biopsy needle to a target site. The medical device can include an elongate member that defines an elongate member lumen within which the biopsy needle can extend. The biopsy needle can define a biopsy needle lumen within which the imaging device can be disposed. The imaging device can be extendable within the biopsy needle lumen to a distal tip of the biopsy needle allow for navigation to target site within a patient. The imaging device can also be retractable within the biopsy needle lumen to allow for the resection of a sample from a target site into the biopsy needle.

The elongate member can have an elongate member opening located at a distal end of the elongate member. When the medical device is at the target site, the elongate member opening can be adjacent to the target site. Furthermore, a biopsy needle deployment feature can either be disposed within the elongate member lumen or proximate the elongate member opening. The biopsy needle deployment feature can be movable between a first configuration and a second configuration.

Figure 1A:
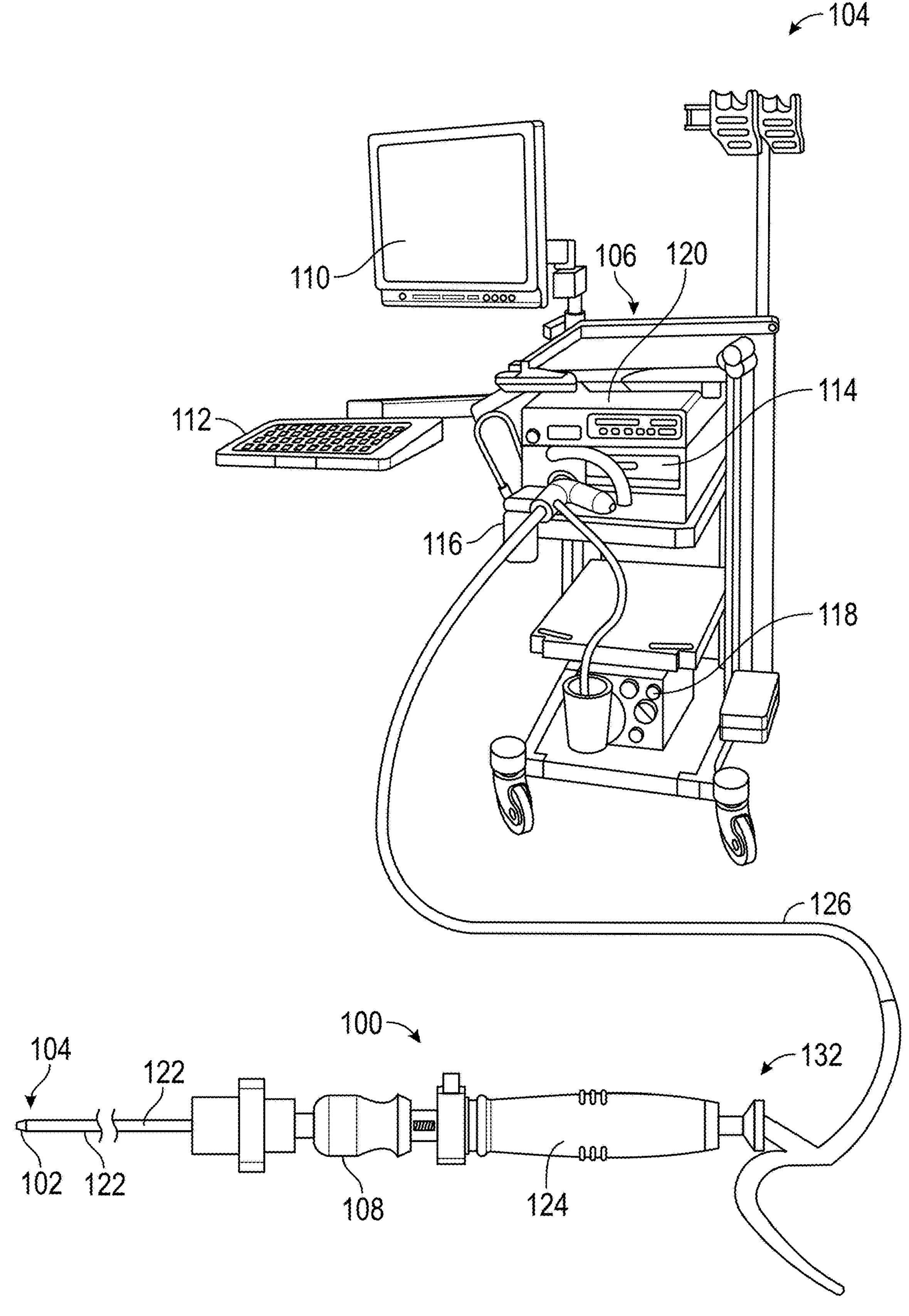
FIGS. 1A and 1B are schematics that illustrate a medical device and a system that can be used to collect a sample from a target site, in accordance with some examples.

FIG. 1A illustrates a medical device 100 that can be used to collect a sample from a target site. The sample can be a tissue sample that is to be subjected to a biopsy procedure. The medical device 100 can include a forward facing guidewire mounted visualizer 102. FIG. 1A also illustrates a system 104 for the medical device 100 that can include an imaging and control system 106. The system 104 is an illustrative example of a system suitable for use with the devices and methods described herein, such as a bronchoscope with an integrated stabilizer or cannulation elements.

The medical device 100 can be insertable into a target site for imaging or to provide passage of or attachment to (e.g., via tethering) one or more sampling devices for biopsies, or one or more therapeutic devices for treatment of a disease state associated with the target site. The medical device 100 can interface with and connect to the imaging and control system 106. The medical device 100 can also include a duodenoscope, though other types of endoscopes can be used with the features discussed herein. The imaging and control system 106 can include an output unit 110, an input unit 112, a light source 114, a fluid source 116, a suction pump 118, and a control unit 120.

The imaging and control system 106 can include various ports for coupling with the system 104. For example, the control unit 120 can include a data input/output port for receiving data from and communicating data to the medical device 100. The light source 114 can include an output port for transmitting light to the medical device 100, such as via a fiber optic link. The fluid source 116 can include a port for transmitting fluid to the medical device 100. The fluid source 116 can include, for example, a pump and a tank of fluid or can be connected to an external tank, vessel or storage unit. A suction pump can include a port used to draw a vacuum from the medical device 100 to generate suction, such as for withdrawing fluid from the target site into which the medical device 100 is inserted and withdrawing samples from a target resected from the target with a resection element. The output unit 110 and the input unit 112 can be used by an operator of the system 104 to control functions of the system 104 and view output of the medical device 100. The control unit 120 can additionally be used to generate signals or other outputs for treating the target site into which the medical device 100 is inserted. The control unit 120 can generate electrical output, acoustic output, a fluid output and the like for treating the target site with cauterizing, cutting, freezing, and the like.

The control unit 120 can include an imaging engine that can receive signal data from sensors at the guidewire mounted visualizer 102. The imaging engine can process the received ultrasound signal data to produce real-time ultrasound images for display on the output unit 110. While the control unit 120 is described as having this functionality, the system 104 can include separate componentry that provides an imaging engine and the functionality described herein.

Figure 1B:
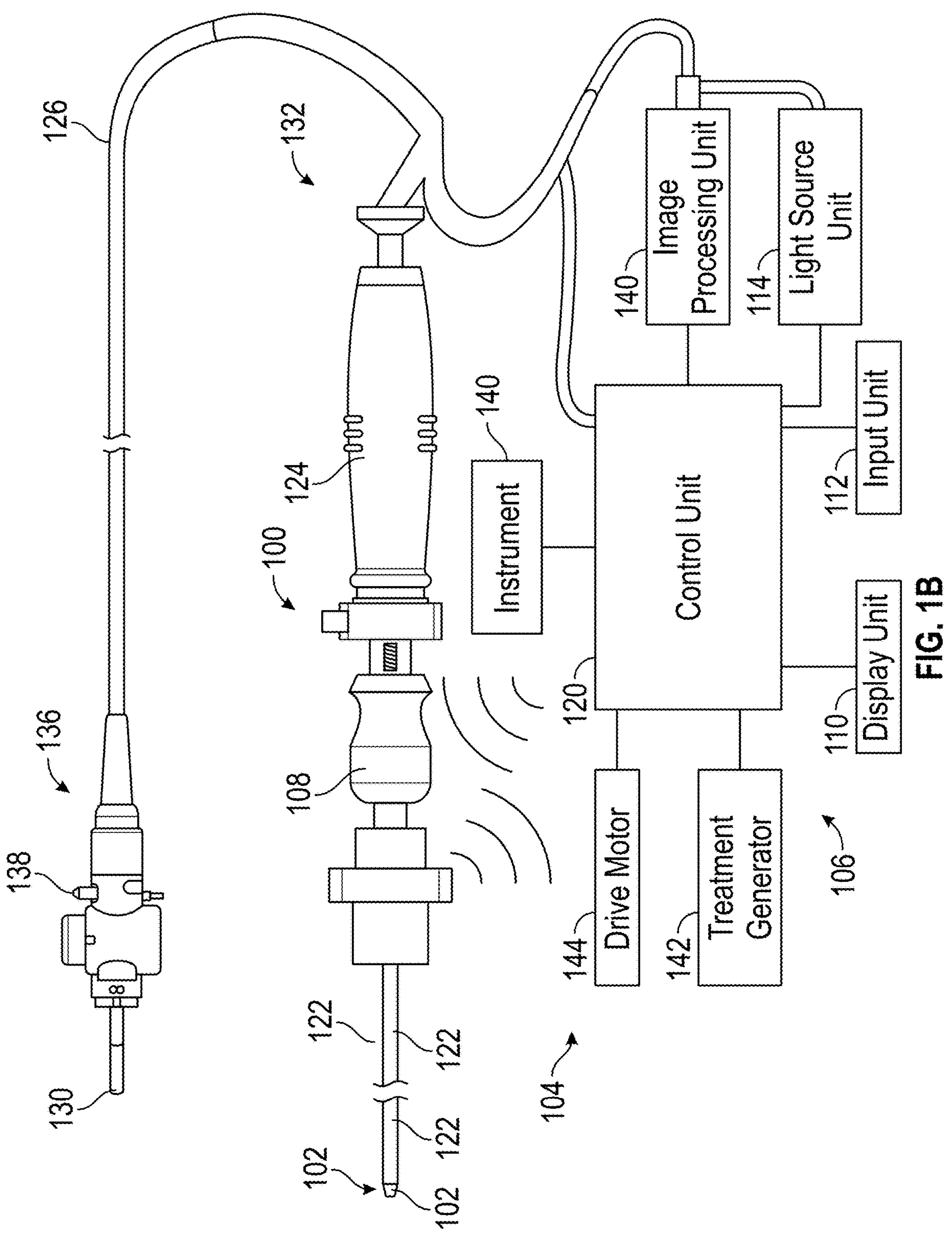

The medical device 100 can include an elongate member 122, a handle 124, which can be coupled to a cable section 126, and a coupler section 136 (FIG. 1B). The elongate member 122 can extend distally from the handle 124 to the guidewire mounted visualizer 102 and the coupler section 136 (FIG. 1B) can extend proximally from the handle 124. The elongate member 122 can include a bending section, and a distal end to which the guidewire mounted visualizer 102 can be attached. The bending section can be controllable (e.g., by a control knob on the handle 124) to maneuver the distal end through tortuous lumen passageways (e.g., stomach, duodenum, kidney, lungs, ureter, etc.). The elongate member 122 can also include one or more working channels (e.g., an internal lumen) that can be elongate and can support insertion of one or more therapeutic tools of the guidewire mounted visualizer 102. The working channel can extend between the handle 124 and the guidewire mounted visualizer 102. Additional functionalities, such as fluid passages, guide wires, and pull wires can also be provided by the elongate member 122 (e.g., via suction or irrigation passageways, or the like).

The coupler section 136 can be connected to the control unit 120 to connect the medical device 100 to multiple features of the control unit 120, such as the input unit 112, the light source unit 114, the fluid source 118, and the suction pump.

The handle 124 can include a knob as well as a port. The knob can be connected to a pull wire, or other actuation mechanisms, extending through insertion the elongate member 122. The port, as well as other ports, can be configured to couple various electrical cables, guide wires, auxiliary scopes, tissue collection devices, fluid tubes, and the like to the handle 124, such as for coupling with the elongate member 122.

The imaging and control system 106 can be provided on a mobile platform (e.g., a cart 130) with shelves for housing the light source 114, the suction pump, an image processing unit 140, etc. Alternatively, several components of imaging and the control system 106 can be provided directly on the medical device 100 so as to make the endoscope “self-contained.”

FIG. 1B is a schematic diagram of the system 104 including the imaging and control system 106 of FIG. 1. The control unit 120 can include or can be coupled to the image processing unit 140, a treatment generator 142, and a drive unit 144, as well as the light source 114, the input unit 112, and the output unit 110. The control unit 120 can include, or can be in communication with, a surgical instrument, which can include a device configured to engage tissue and collect and store a portion of that tissue and through which imaging equipment (e.g., a camera) can view target tissue via inclusion of optically enhanced materials and components. The control unit 120 can be configured to activate a camera to view target tissue distal of the system 104 and the medical device 100. Likewise, the control unit 120 can be configured to activate the light source unit 114 to shine light on the surgical instrument, which can include select components that are configured to reflect light in a particular manner, such as tissue cutters being enhanced with reflective particles. The light source 114 can be controlled to illuminate a target site using light of a desired spectrum (e.g., broadband white light, narrow-band imaging using preferred electromagnetic wavelengths, and the like).

The coupler section 136 can be connected to the control unit 120 to connect the medical device 100 to multiple features of the control unit 120, such as the image processing unit 140 and the treatment generator 142. In examples, instruments and devices can be independently connected to the control unit 120 via the cable section 126.

The image processing unit 140 and the light source 114 can each interface with the medical device 100 by wired or wireless electrical connections. The imaging and control system 106 can accordingly illuminate a target site, collect signals representing the target site, process signals representing the target site, and display images representing the target site on the display unit 110. The imaging and control system 106 can connect (e.g., via an endoscope connector) to the medical device 100 for signal transmission (e.g., light output from a light source, video signals from an imaging system in the distal end, diagnostic and sensor signals from a diagnostic device, and the like).

The fluid source 116 can be in communication with the control unit 120 and can include one or more sources of air, saline, or other fluids, as well as associated fluid pathways (e.g., air channels, irrigation channels, suction channels) and connectors (barb fittings, fluid seals, valves and the like). The fluid source 116 can be utilized as an activation energy source for a biasing device or a pressure-applying device of features discussed herein. The imaging and control system 106 can also include the drive unit 144, which can include a motorized drive for advancing a distal section of medical device 100.

In a first position, the guidewire mounted visualizer 102 can be forward facing and located at a distal end 130 of the medical device 100. The guidewire mounted visualizer 102 can provide imaging and illumination, such as endoscope visualization, from within a biopsy needle that can be used during various procedures. These procedures can include endobronchial, urological, or any other type of procedure where samples are removed from target sites for testing. Precise navigation to a target site and visualization of an area associated with the target site, such as anatomy associated with the target site, can increase the efficiency of removing samples from the target site. By virtue of being disposed at the distal end 130, the guidewire mounted visualizer 102 can provide precise navigation and visualization for the medical device 100.

The guidewire mounted visualizer 102 can utilize any type of imaging technology that can allow for navigation to a target site, removal of a sample from a target site, and/or identification of a type of sample or material at the target site, such as narrow band imaging, red dichromic imaging (RDI), or the like. The guidewire visualizer 102 can also utilize light pipe technology where the guidewire mounted visualizer 102 can implement a confocal laser endomicroscopy platform, which can allow for cellular visualization at a target site. In spectroscopic applications, the guidewire mounted visualizer 102 can use hyperspectral imaging to identify samples at a target site, such as tissue type and the like. In addition, the guidewire mounted visualizer 102 can implement confocal microscopy techniques to identify samples at the target site.

Figure 2:
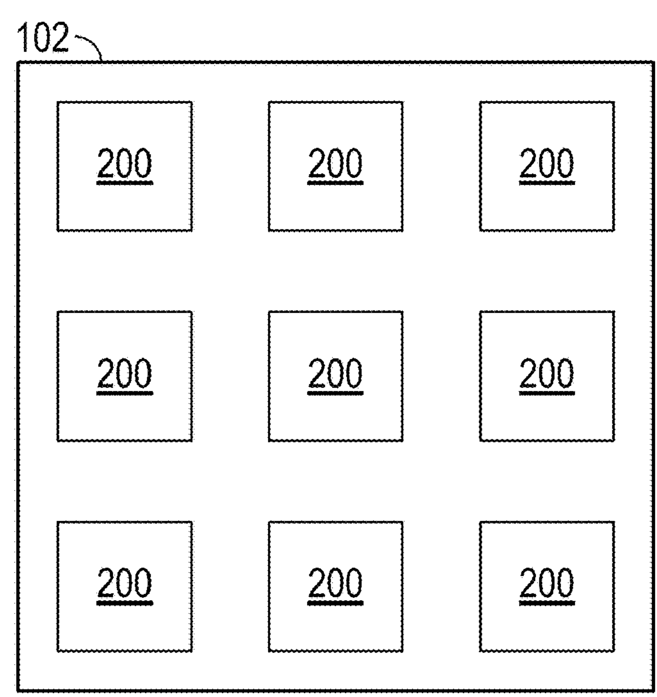
FIGS. 2-4 show a guidewire mounted visualizer of the medical device of FIG. 1, in accordance with some examples.
Figure 3:
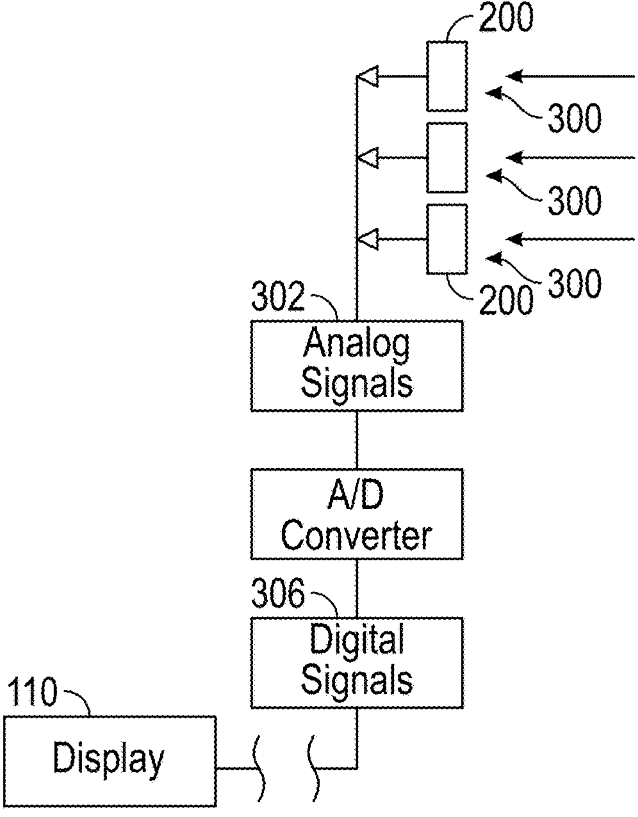
Figure 4:
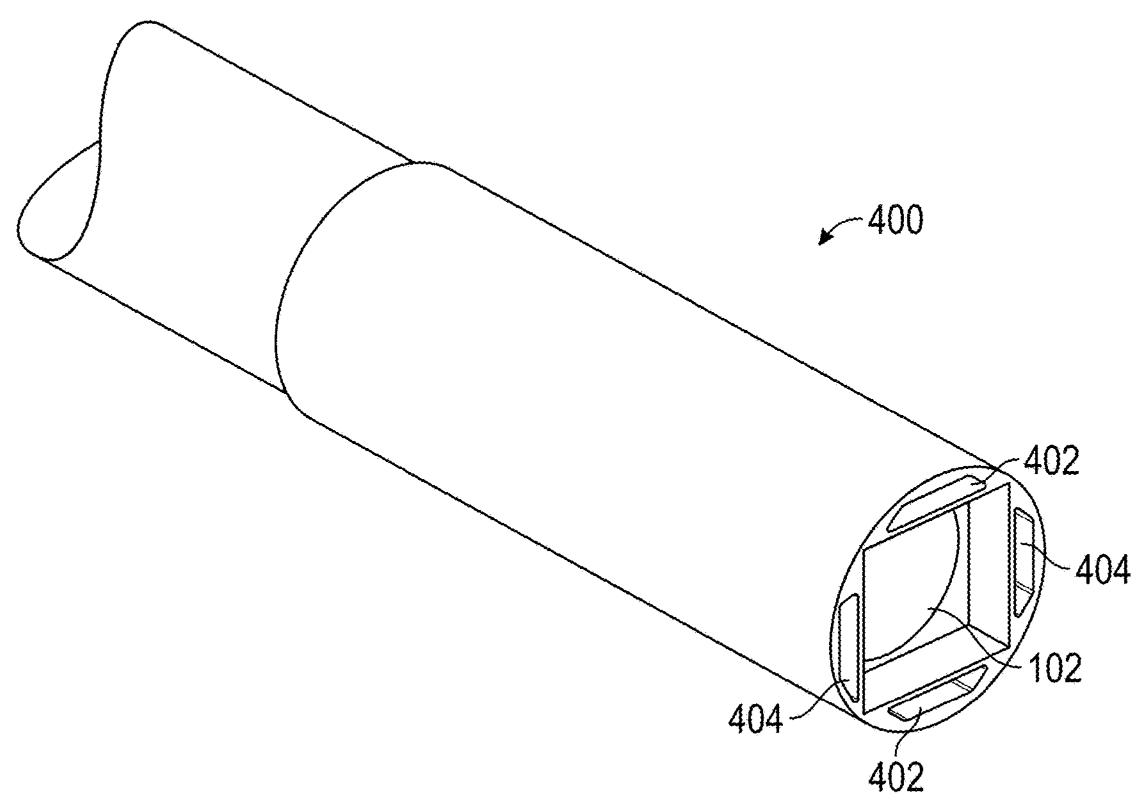

Furthermore, the guidewire mounted visualizer 102 can be an imaging device that can include a chip-on-tip complementary metal-oxide semiconductor (CMOS) sensor. The guidewire mounted visualizer 102 can include an array of pixels 200 as shown in FIG. 2. While a nine-by-nine array of the pixels 200 is shown, the guidewire mounted visualizer 102 can include any number of pixels 200. The pixels 200 can receive photons 300 (FIG. 3) and convert the photons 300 into electrons. The electrons can then be converted to a voltage at each of the pixels 200. Analog signals 302 associated with the voltage can then be multiplexed by row and column and provided to an analog-to-digital converter 304. The analog-to-digital converter 304 can then output digital signals 306 for display at the output unit 110.

Furthermore, the guidewire mounted visualizer 102 can be any other type of image capture device capable of fitting in a small area, such as the distal end 130 of the medical device 100. The guidewire mounted visualizer 102 can be part of an assembly 400 that includes illumination feature 402. The illumination feature 402 can implement fiber optics that can illuminate an area being viewed by the guidewire mounted visualizer 102. The illumination feature 402 can also be light emitting diodes or can include any other type of device capable of illuminating an area being viewed by the guidewire mounted visualizer 102.

The assembly 400 can also include ports 404. The ports 404 can include illumination features similar to the illumination feature 402. Alternatively, the ports 404 can be fluidly coupled to the suction pump 118 such that a vacuum can be created at the distal end 130 during removal of a sample from a target site via the ports 404.

The medical device 100 can include a catheter assembly 500 where the guidewire mounted visualizer 102 can be disposed within a biopsy needle 502 of the catheter assembly 500 in the first position. The biopsy needle 502 can be extendable and retractable within an elongate member lumen 504. The biopsy needle 502 can include a biopsy needle lumen 506. The guidewire mounted visualizer 102 can be mounted on a distal end 508A of a guidewire 508 deployed within the biopsy needle 502. The guidewire 508 can extend between the guidewire mounted visualizer 102 and a proximal end 132 of the medical device 100. Since the guidewire mounted visualizer 102 is mounted on the guidewire 508, the guidewire mounted visualizer 102 can axially move within the biopsy needle 502, the elongate member lumen 504, and the biopsy needle lumen 506 along a direction X and along a direction Y.

Figure 5A:
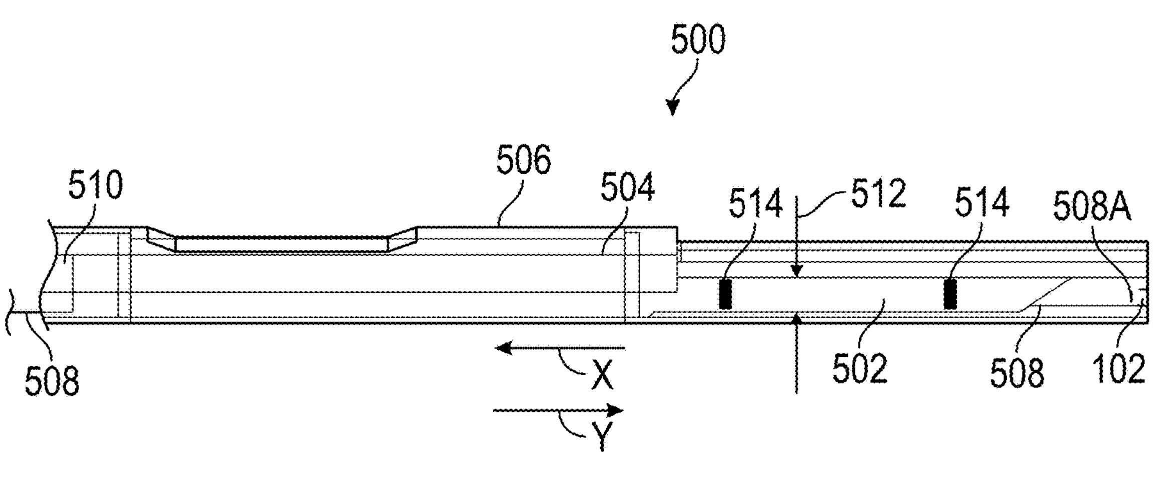
FIGS. 5A and 5B are schematics of the guidewire mounted visualizer of the medical device of FIG. 1, in accordance with some examples.
Figure 5B:
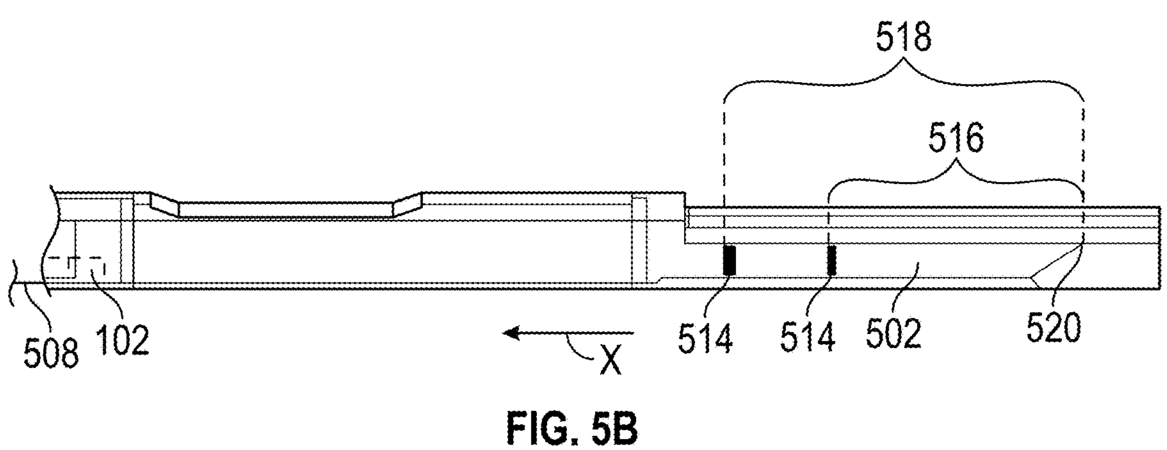

A practitioner can move the guidewire 508 along the direction Y to move the guidewire mounted visualizer 102 into the first position. Moreover, a practitioner can move the guidewire 508 along the direction X to move the guidewire mounted visualizer 102 into a second position, as shown in FIG. 5B. The guidewire mounted visualizer 102 can be located in the second position when the biopsy needle 502 is used to resect a sample from a target site, as will be discussed further on. The medical device 100 can also include a needle slider 108 at the handle 124. The handle 124 can have a wire drive system that, in conjunction with the needle slider 108, can function to move the biopsy needle 502 axially along the directions X and Y. The elongate member 122 can define a lumen 510 through which the biopsy needle 502, the elongate member lumen 504, the biopsy needle lumen 506, and the guidewire 508 can extend. The assembly 300 can have a diameter 512 that allows for fitment in the anatomy within a patient. The diameter 512 can be in a range of about 1.5 mm to about 2.5 mm, about 1.7 mm to about 2.3,and have a value of about 1.9 mm.

The biopsy needle 502 can also include landmarks 514, which can be used to determine an amount of a sample within the biopsy needle 502. In particular, when a sample is resected into the biopsy needle 502, the guidewire mounted visualizer 102 can be used to determine when the resected sample is at one of the landmarks 514. The landmarks 514 can be at a known distance 516/518 from a distal tip 520 the biopsy needle 502. The distance 516/518 in conjunction with the internal diameter 512 can be used to calculate a volume of a resected sample within the biopsy needle 502.

The catheter assembly 500 can also include a sensor 600 and electromagnetic elements 602 at the distal end 130 and near the guidewire mounted visualizer 102 when the guidewire mounted visualizer 102 is in the first position. The sensor 600 can be used to create a field of view of a target site from a which a sample can be collected. The sensor 600 can include an array that can convert electrical signals into ultrasound signals and convert reflected ultrasound signals into electrical signals. The converted electrical signals can be sent to an imaging engine coupled with the medical device 100 that can be used to image a target and create a field of view for display on a display unit.

The sensor 600 can be a piezoelectric micromachined ultrasonic transducer (PMUT), a capacitive micromachined ultrasonic transducer (CMUT), or a polymer-based CMUT. When the sensor 600 is a PMUT, the sensor 600 can include a flexible substrate, an ultrasound transducer array, mixed-signal integrated circuits (IC), and capacitors. The flexible substrate can be a laminated structure having a cover layer, an electrical insulating layer, electrically conductive features, and adhesives. The electrical insulating layer can be made of polyimide having a thickness of about 12 μm. The electrically conductive features can be etched from copper foils having a thickness of about 5 μm, vapor deposited copper having a thickness in a range between about 2 μm and about 4 μm thick, vapor deposited nickel having a thickness in a range between about 2 μm and about 4 μm thick, or vapor deposited gold having a thickness of about 0.5 μm. The flexible substrate can include electrical contacts such as pads for die attachment of components for the mixed-signal ICs and capacitors. The ultrasound transducer array can include an array of 64 elements where each element includes at least one PMUT. The PMUTs can have a resonant frequency between about 5 MHz and about 40 MHz. The PMUTs can also have a resonant frequency of about 9.0 MHz.

When the sensor 600 is a CMUT, the sensor 600 can be formed with a silicon substrate where a cavity can be formed in the silicon substrate. A thin layer can be suspended over the cavity and function as a membrane where a metalized layer can act as an electrode. When an AC signal is applied across the electrode, ultrasonic waves can be produced in a field of view of a target site. The ultrasonic waves can be used to determine a location of a target within a field of view.

The electromagnetic elements 602 can include coils and can track a trajectory of the biopsy needle 502 within a field of view created by the sensor 600 within a target site. The electromagnetic elements 602 can have lead wires that extend into the biopsy needle lumen 506, through the biopsy needle lumen 506, and to a power source.

Figure 7:
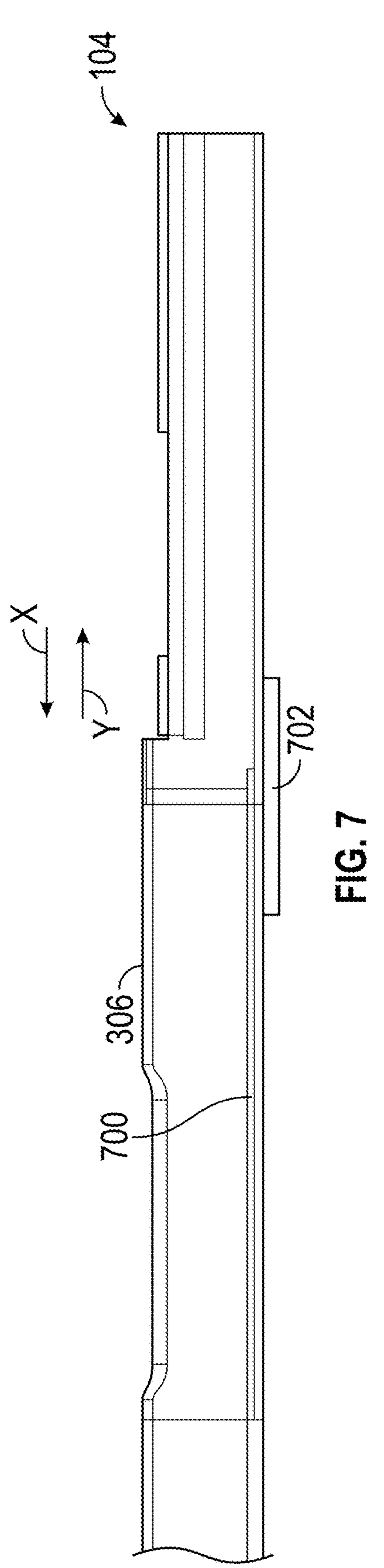
FIGS. 7 and 8A-8C illustrate a biopsy deployment feature of the medical device of FIG. 1, in accordance with some examples.

A biopsy deployment feature 700 can be located within the biopsy needle lumen 506. The biopsy deployment feature 700 can function to deploy the biopsy needle 502 from the biopsy needle lumen 506. In a first position, the biopsy deployment feature 700 can have a substantially flat orientation as shown in FIG. 7 such that the biopsy needle 502 can extend over the biopsy deployment feature 700 and to the distal end 130 within the biopsy needle lumen 506. Moreover, when the biopsy deployment feature 700 has the orientation shown in FIG. 7, the guidewire mounted visualizer 102 can axially move along the directions X and Y within the biopsy needle lumen 506 along with the assembly 500 and into the first position.

Figure 8A:
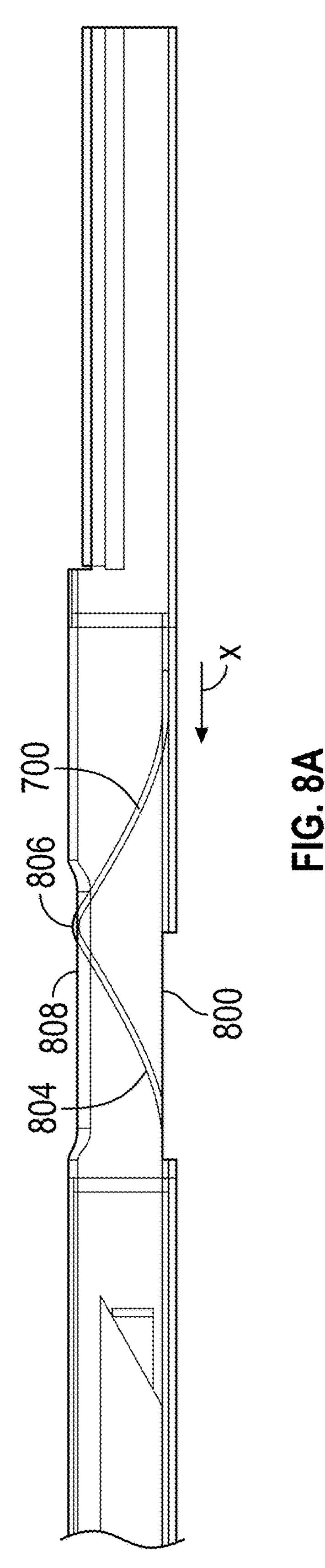
Figure 8B:
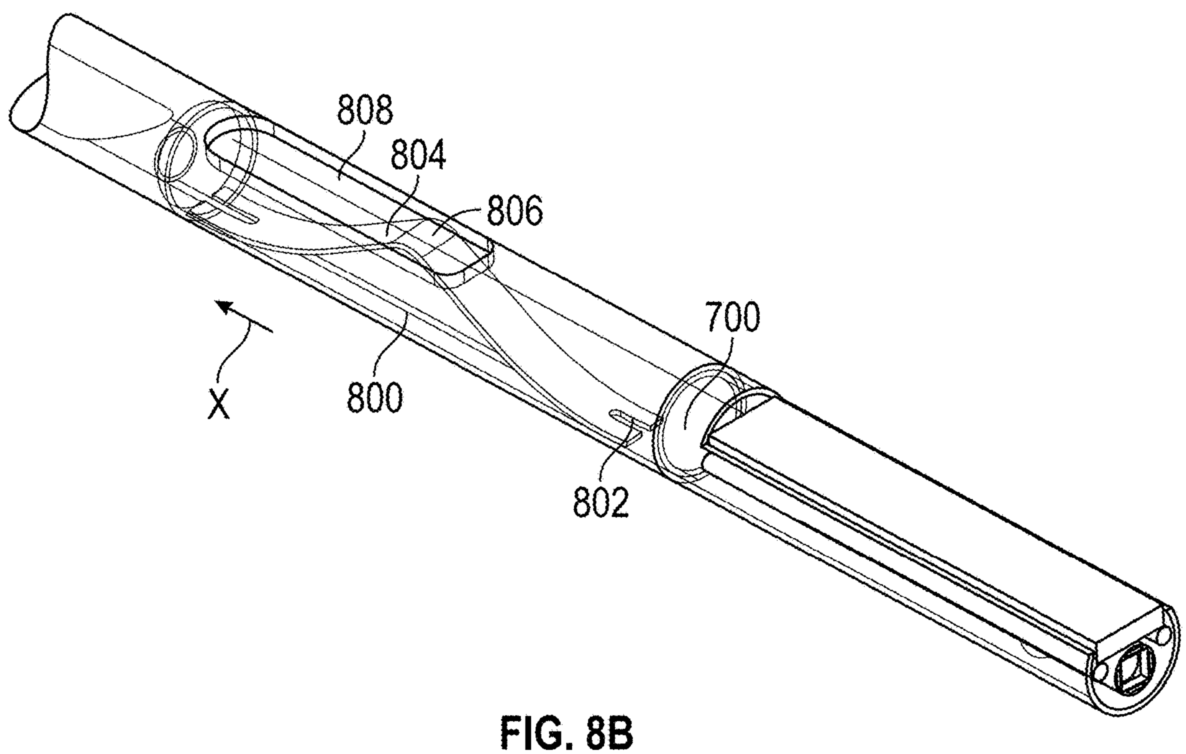
Figure 8C:
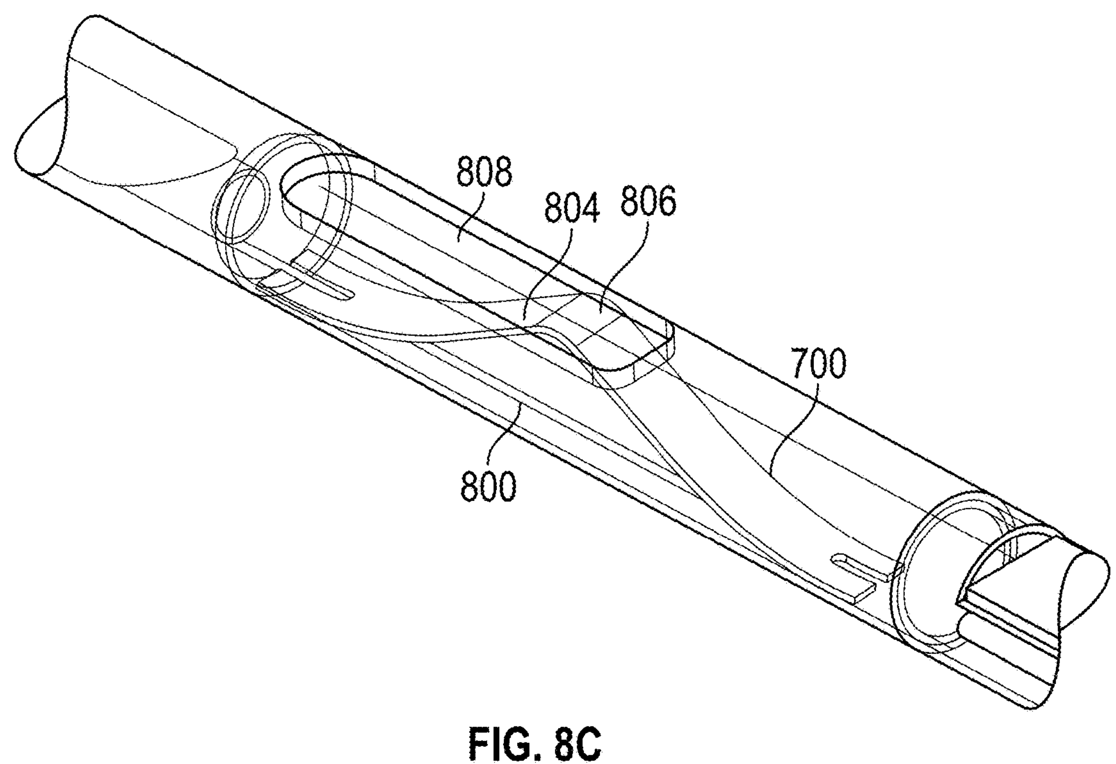

An actuator mechanism 800 can extend within the biopsy needle lumen 506 and couple with the biopsy deployment feature 800 at an end 802. The actuator mechanism 800 can be a guidewire such that when a practitioner moves the actuator mechanism 800 along the direction X, the biopsy deployment feature 700 can move into a deployed configuration and form a deployment ramp 804 as shown in FIGS. 8A-8C where the biopsy deployment feature 800 can have an inverted "V" shape.

In further examples, the actuator mechanism 800 can be formed of a phase change material, such as Nitinol memory wire, that can undergo a change in length along the direction X when electric current is applied to the actuator mechanism 800. When the actuator mechanism 800 is formed of a phase change material and electric current is applied, the biopsy deployment feature 700 can move into the deployed configuration.

In further examples, the actuator mechanism 800 can include a piezoelectric film disposed at a bottom surface. Here, when a voltage is applied to the piezoelectric film, the piezoelectric film can contract, causing the formation of the deployment ramp 804.

In further examples, the actuator mechanism 800 can be a rigid member attached at a proximal end of the deployment ramp 804. When the actuator mechanism 800 is moved along the direction Y, the movement can cause the biopsy needle deployment feature 700 to have the configuration shown with reference to FIGS. 8A-8C.

When the biopsy deployment feature 700 forms the deployment ramp 804, a peak 806 of the biopsy deployment feature 700 can jut out from an elongate member opening 808. The biopsy deployment feature 700 can have an inverted "V" shape at the elongate member opening 808. As will be discussed further on, the deployment ramp 804 can be used to place a needle, such as the biopsy needle 502, into a target site for resection of a sample from the target site.

Figure 6:
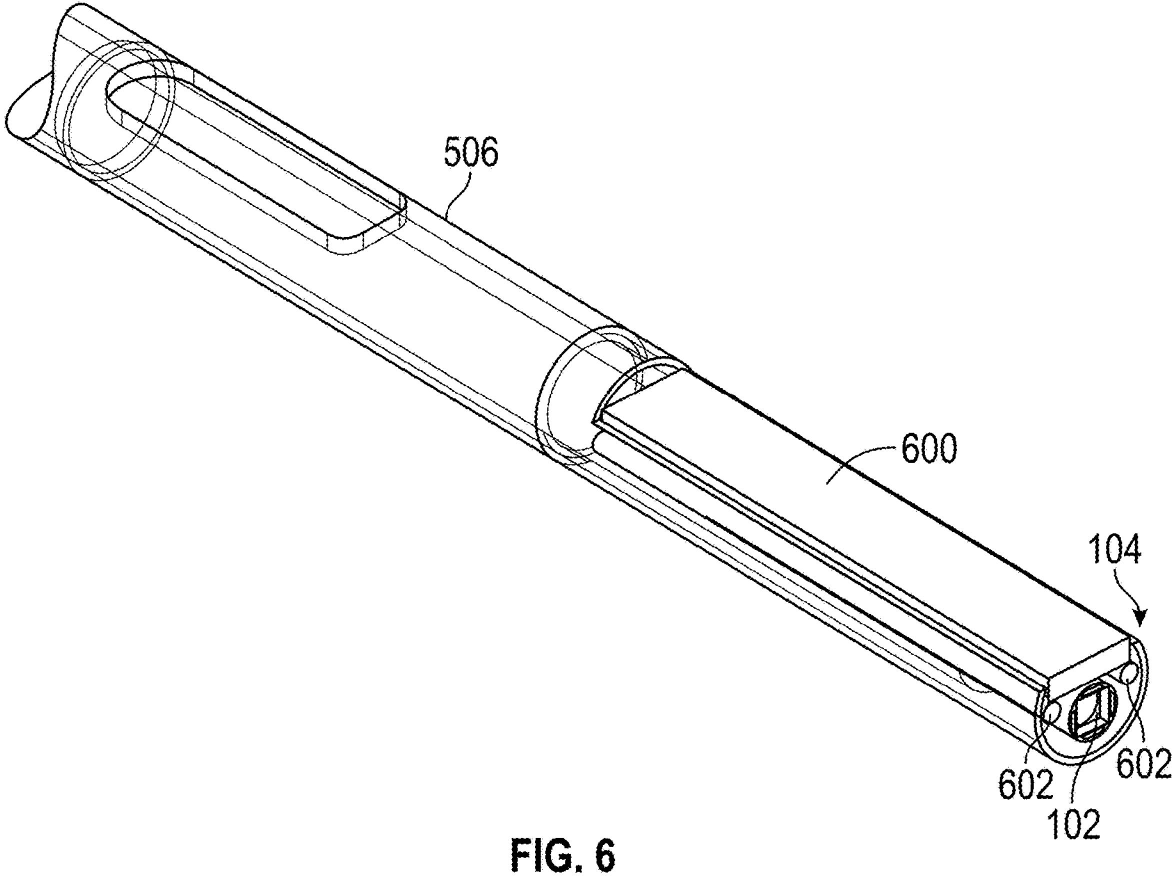
FIG. 6 illustrates a sensor of the guidewire mounted visualizer of the medical device of FIG. 1, in accordance with some examples.

The biopsy deployment feature 700 can be formed from a pliable alloy that allows the biopsy deployment feature 700 to repeatedly change between the substantially flat orientation of FIG. 6 and the deployed configuration of FIGS. 7A-C, such as Nitinol, a blue tempered spring steel, or the like. The biopsy deployment feature 700 can be formed from spring steel or a similar material in order to allow switching between the two configurations.

The biopsy needle lumen 506 also can include an inflation cuff 702 that can be inflated during use of the medical device 100. The inflation cuff 702 may be any type of device capable of inflating when filled with a fluid, such as a syringe-style, multiple-use balloon dilator, or the like.

Figure 9:
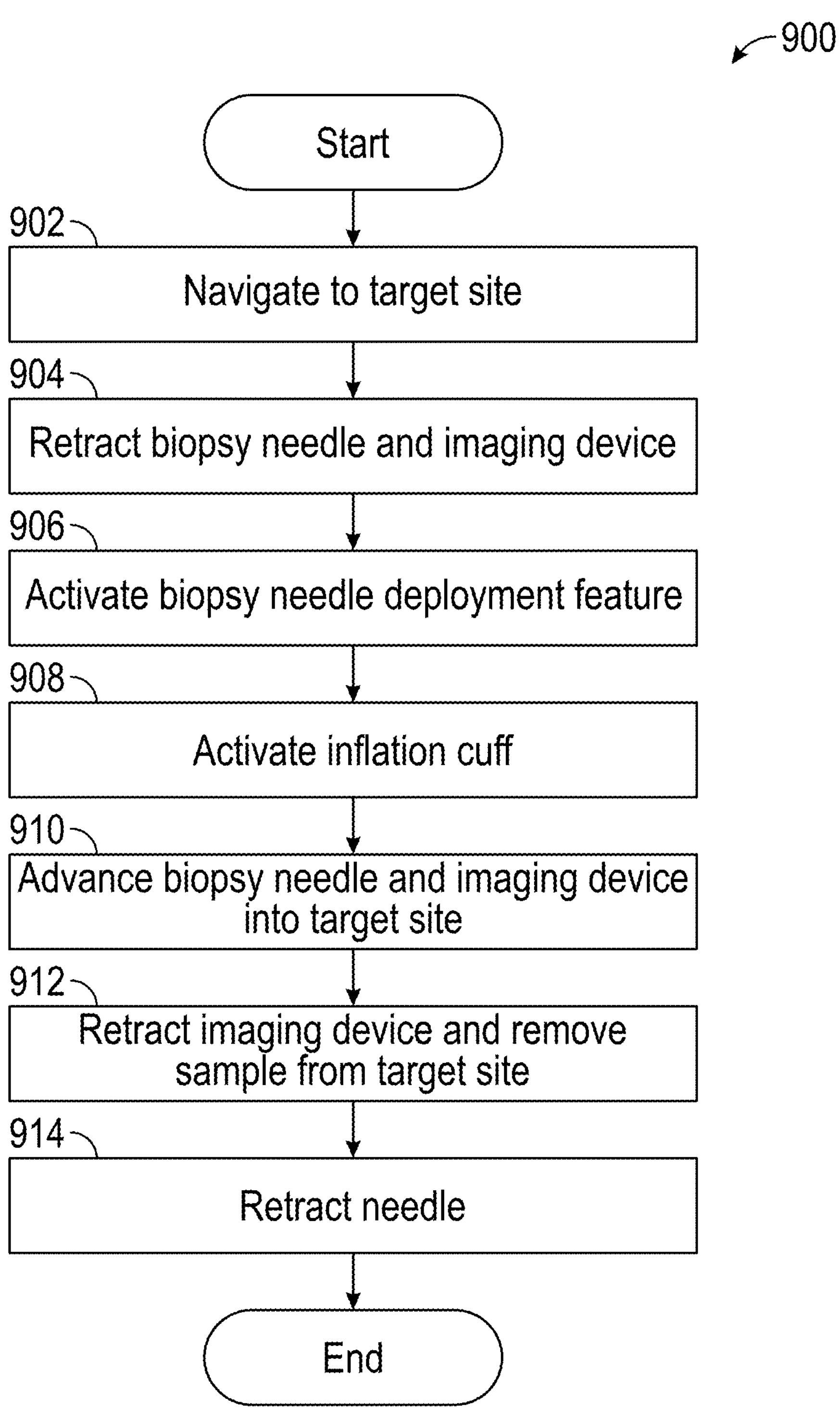
FIG. 9 is a method of using the medical device of FIG. 1, in accordance with some examples.
Figure 10:
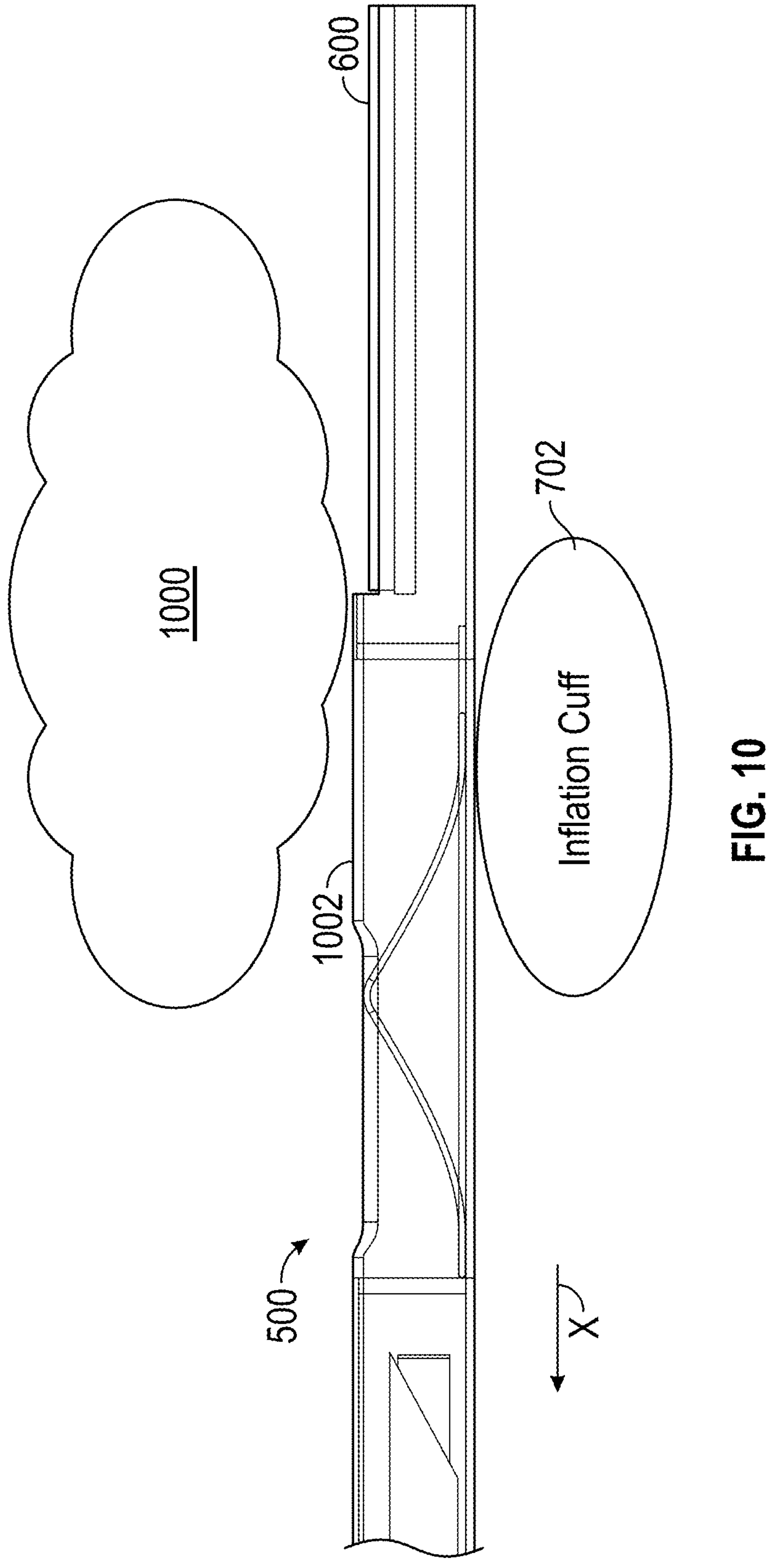
FIGS. 10, 11, 12A, and 12B show using the medical device of FIG. 1 according to the method in FIG. 9, in accordance with some examples.

Now making reference to FIG. 9, a method 900 for acquiring a sample from a target site 1000 using the catheter assembly 500 having the guidewire mounted visualizer 102 is shown. Scans of a patient and pathways that are superimposed on the patient scans can be used to navigate to the target site 1000 with the catheter assembly 500. During an operation 902, after extending the biopsy needle and the imaging device to a distal tip of the medical device, a practitioner can use the guidewire mounted visualizer 102 to navigate pathways in a patient to a target site 1000 and place the catheter assembly 500 at the target site 1000. During the operation 902, the guidewire mounted visualizer 102 can provide visualization of the pathways traversed by the catheter assembly 500. In particular, the guidewire mounted visualizer 102 can be in the first position, thereby allowing endoscope visualization and forward-looking images of the navigated anatomy. Moreover, the practitioner can determine when the catheter assembly 500 has arrived at the target site 1000 with the guidewire mounted visualizer 102.

Once the needle system 300 is at the target site 1000, an operation 904 can be performed where the biopsy needle 502 and the guidewire mounted visualizer 102 are retracted from the first position and into the second position. During the operation 904, the biopsy needle 502 and guidewire mounted visualizer 102 can be moved into a third position as shown in FIG. 8A, where each of the biopsy needle 502 and the guidewire mounted visualizer 102 are moved past the elongate member opening 808. The biopsy needle 502 can be moved with the needle slider 108 and the handle 124 while the guidewire mounted visualizer 102 can be moved with the guidewire 508.

In an operation 906, the deployment ramp 804 can be deployed after the biopsy needle 502 and the guidewire mounted visualizer 102 are moved into the third position. The actuator mechanism 800 can be applied to the biopsy needle deployment feature 700 to form the deployment ramp 804 during the operation 906 such that the catheter assembly 500 has the configuration of FIGS. 8A-C using any of the techniques discussed above where the biopsy needle deployment feature 700 can move from the position in FIG. 7 to the position in FIGS. 8A-8C. The inflation cuff 702 can then be activated during an operation 908 by providing a fluid, such as a gas or a liquid, to the inflation cuff 702, in order to inflate the inflation cuff 702 into the configuration of FIG. 9. The inflation cuff 702 can be activated until a surface 1002 of the catheter assembly 500 contacts a surface of the target site 1000. Furthermore, the inflation cuff 702 can be activated until the sensor 600 contacts the target site 1000.

Figure 11:
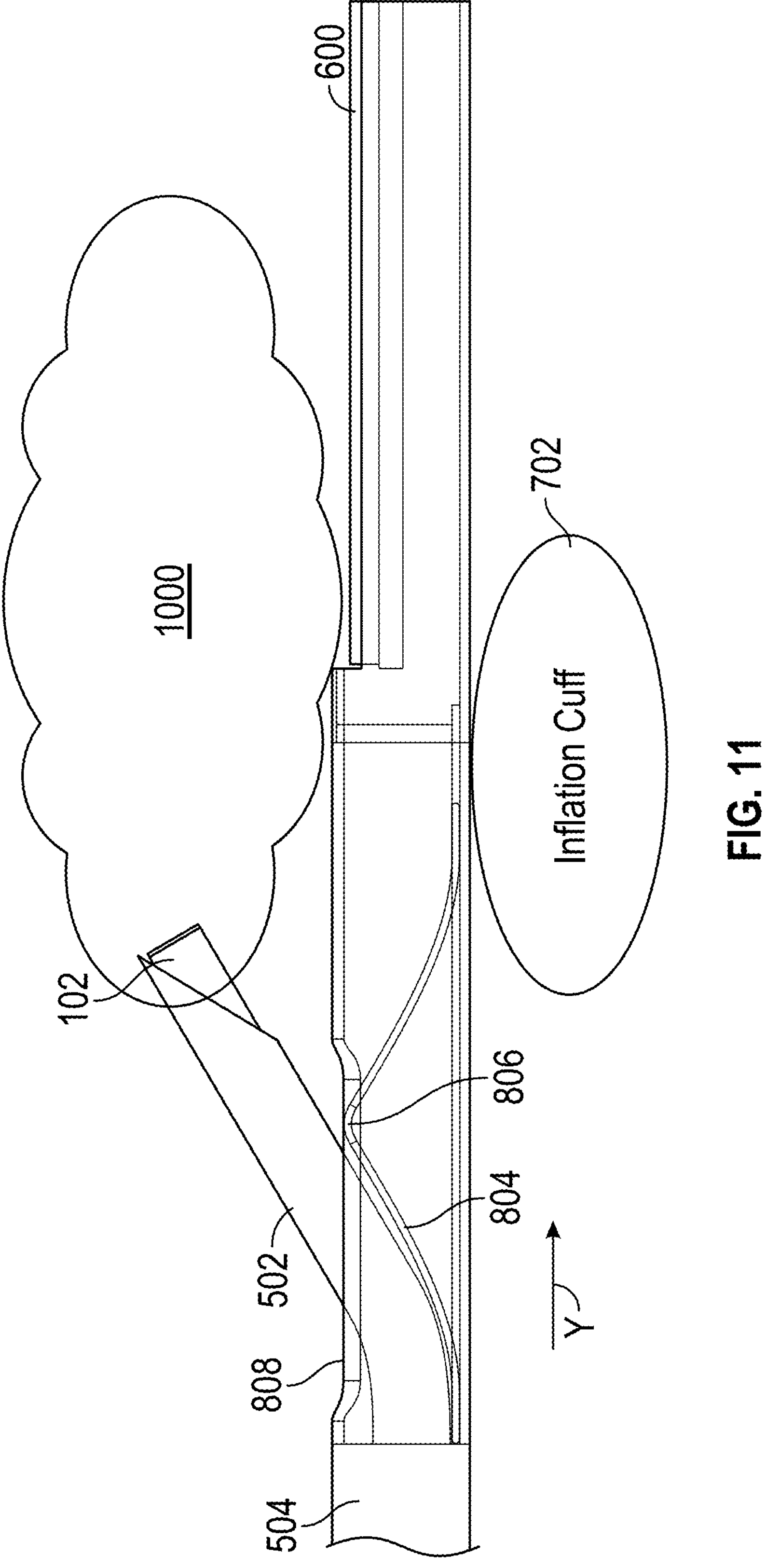

Upon activation of the inflation cuff during the operation 908, the biopsy needle 502 and the guidewire mounted visualizer 102 are advanced into the target site 1000 during an operation 910. During the operation 910, a practitioner can move the needle slider 108 and the handle 124 along the direction Y until both the biopsy needle 502 and the guidewire mounted visualizer 102 advance up the deployment ramp 804, past the peak 806 and the elongate member opening 808 and into the target site 1000, as shown in FIG. 11. Here, the guidewire mounted visualizer 102 can function to prevent tissue from entering into the biopsy needle 502 prior to the biopsy needle 502 being positioned within the target site 1000 where the tissue sample is to be removed.

After the biopsy needle 502 and the guidewire mounted visualizer 102 are advanced into the target site 1000, the guidewire mounted visualizer 102 is retracted from the target site 1000 using the guidewire 508 during an operation 912. In addition, a sample is removed from the target site 1000 using the biopsy needle 502. Where the target site 1000 corresponds to anatomy and the sample corresponds to tissue, a tissue sample can be removed from the target site 1000 using the biopsy needle 502 during the operation 912 after the guidewire mounted visualizer 102 is retracted. The biopsy needle 502 can include a cutting surface, which can resect the tissue sample. Additionally, the biopsy needle 502 can be fluidly coupled to the suction pump 118 via the ports 404 such that when the tissue sample is resected, the suction pump 118 and the ports 404 can pull the tissue sample from the target site 1000.

By virtue of having the guidewire mounted visualizer 102 mounted within the biopsy needle 502, during removal of the tissue sample, a practitioner can view the removal of the tissue sample in real-time. Furthermore, during retraction of the biopsy needle 502 from the target site 1000 and from a patient, the guidewire mounted visualizer 102 allows a practitioner to ensure that the removed tissue sample remains within the biopsy needle 502.

Figures 12A, 12B:
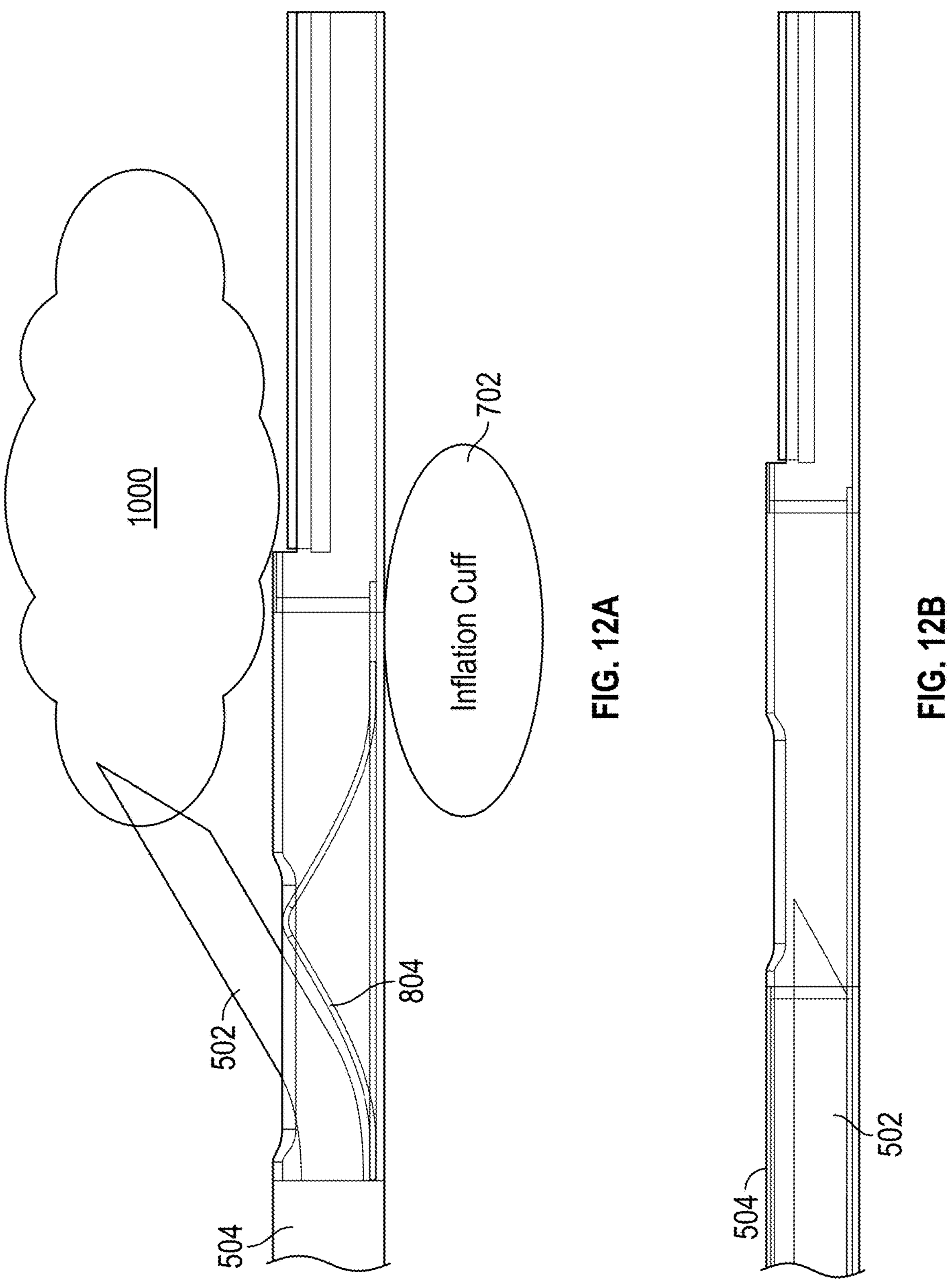

Once the sample is removed from the target site in the operation 912, the biopsy needle 502 is retracted from the target site 1000 and into the elongate member lumen 504 during an operation 914, as shown in FIGS. 12A and 12B.

Elements of the catheter assembly 500 can be modified from that described above. To further illustrate, the catheter assembly 500 could include a biopsy needle with a catheter-based guide wire disposed within the biopsy needle 502. A biopsy needle having this configuration could be delivered through a working channel of a scope of the medical device 100 thereby avoiding the necessity of the elongate member opening 808.

The needle sheath can be configured to create a vacuum upon extraction from a target site. The needle sheath can include piston rings disposed about an outer periphery thereof that can engage with surfaces of the target site. When the needle sheath is extracted from the target site, such as after performing the operation 914, by virtue of the piston rings engaging with surfaces of the target site, a vacuum can be created, thereby pulling additional samples from the target site where suction applied to the needle can draw in the additional samples.

Figures 13, 14:
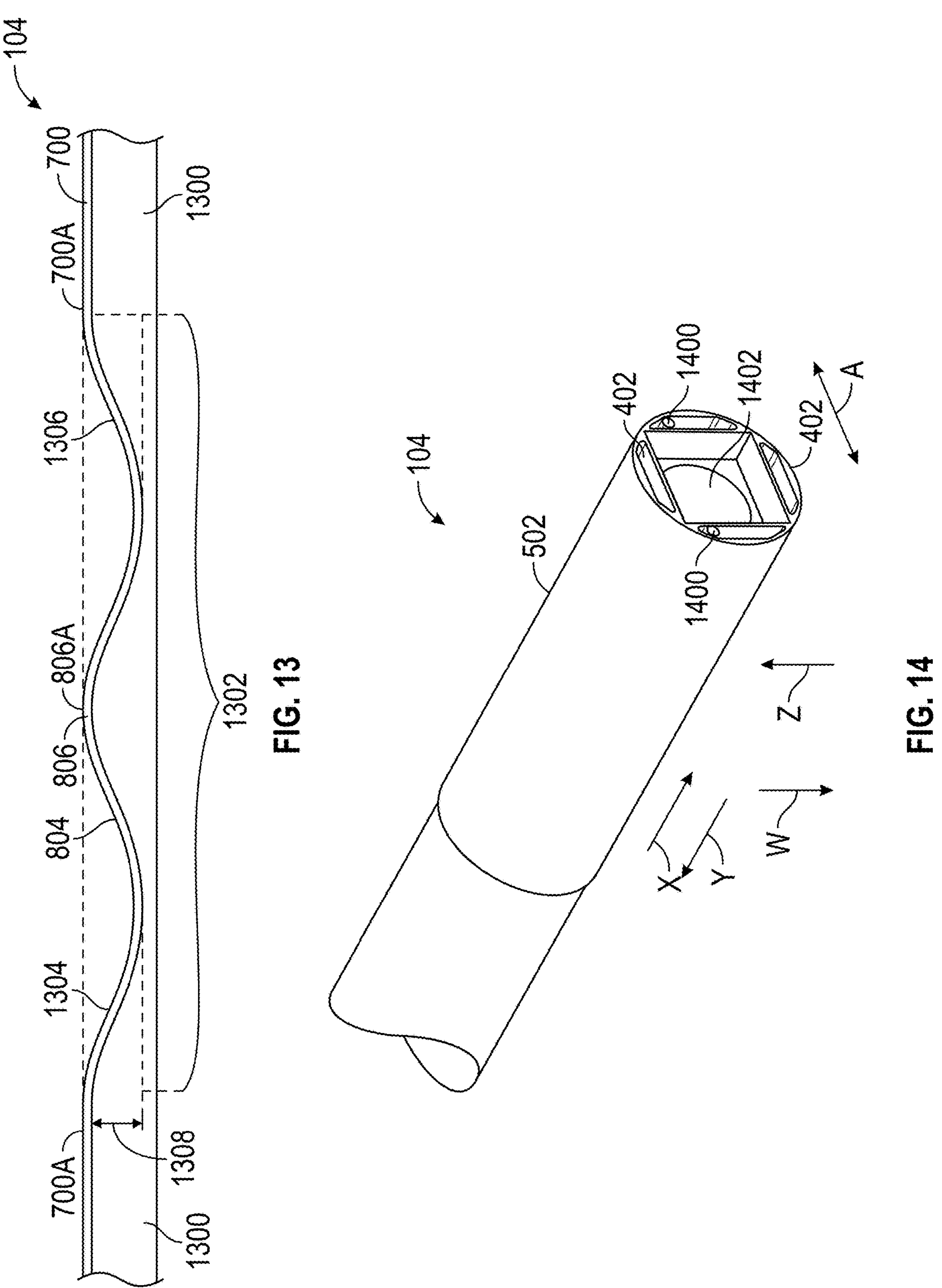
FIG. 13 shows an alternative example of the medical device of FIG. 1, in accordance with some examples.
FIG. 14 shows an alternative example of the medical device of FIG. 1, in accordance with some examples.

Alternatively, the biopsy needle deployment feature 700 can be formed such that in a nominal state, the peak 806 can be formed as shown in FIG. 13 where the biopsy needle deployment feature 700 can be pre-bent. Here, a portion 1300 of the distal end 130 of the medical device 100 can have a recess 1302 within which sloped portions 1304 and 1306 of the biopsy needle deployment feature 600 can be disposed. The sloped portions 1304 and 1306 can slope in an upward direction Z towards the peak 806 such that when a compressive force is applied to the actuator mechanism 800 along the direction Y, the actuator mechanism 800 and the peak 806 can have the configuration shown with reference to FIGS. 8A-8C. Furthermore, the recess 1302 can be formed to a depth 1308 such that a top surface 700A of the biopsy needle deployment feature 700 and a top surface 806A of the peak 806 can remain planar with each other. This planarity can minimize the possibility of the guidewire mounted visualizer 102 along with the biopsy needle 502 from getting caught on the recess 1302 during use of the medical device 100 as described herein, i.e., the peak 806 does not obstruct the guidewire mounted visualizer 102 and the biopsy needle 502 during use of the medical device 100.

In alternative examples, the medical device 100 can include steerable guidewires 1400 that can be used to steer the distal end 130 through a patient and to a target site. Thus, the steerable guidewires 1400 can form a steerable guidewire mounted visualizer 1402 having the same features as discussed above with reference to the guidewire mounted visualizer 102. The steerable guidewires 1400 can be movable along the direction X and the direction Y. When moved along the directions X and Y, the steerable guidewires 1400 can steer the distal end 130 along directions W and Z. By virtue of having the steerable guidewires 1400 along with the steerable guidewire mounted visualizer 1402, the sensor 700 can be eliminated.

Figure 15:
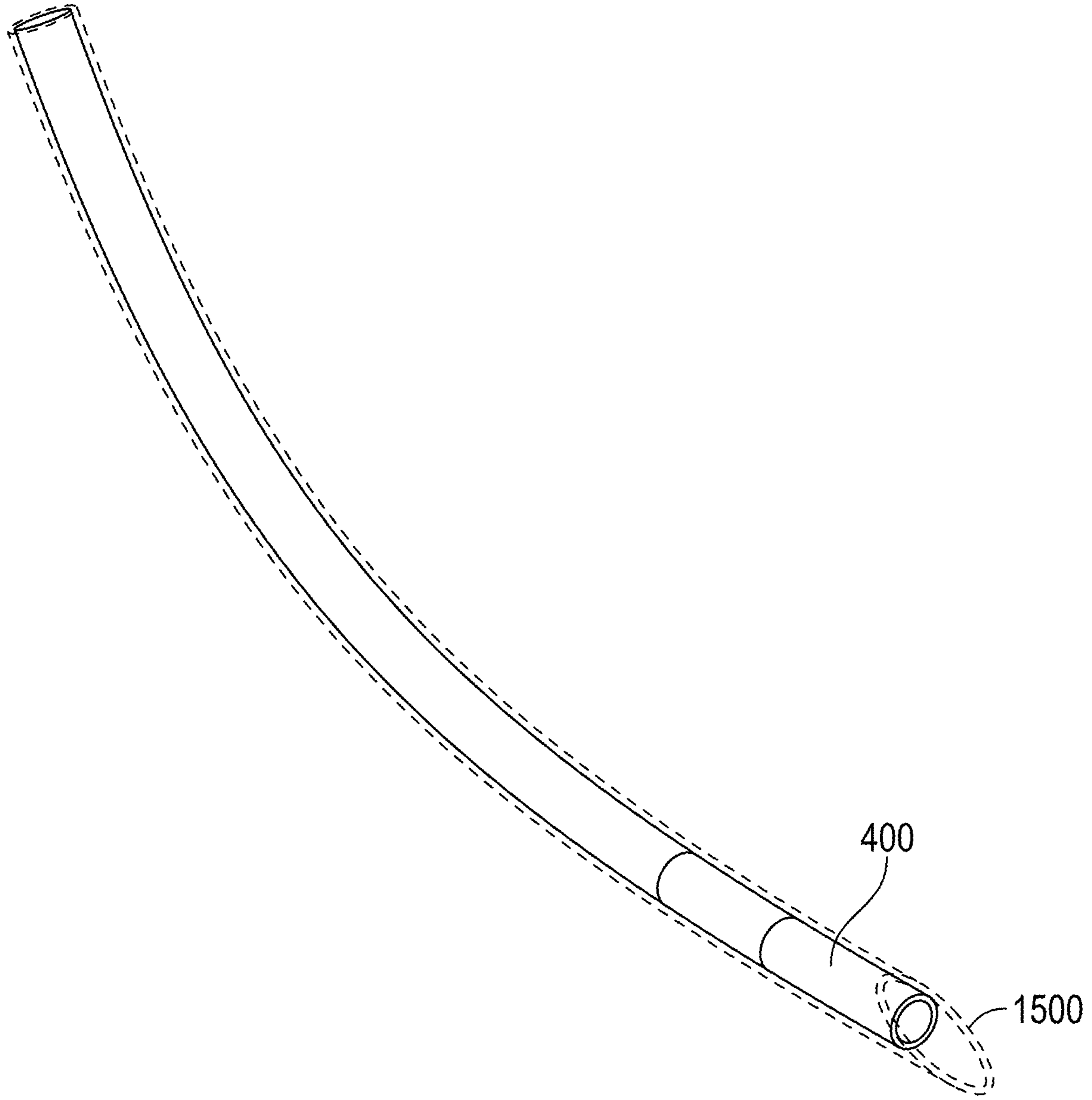
FIG. 15 shows an alternative example of the medical device of FIG. 1, in accordance with some examples.

Now making reference to FIG. 15, an alternative example of the medical device of FIG. 1 is shown. Here, a needle lumen 1500, having the same functionality as the needle lumen 506, is shown.

What is claimed is:

1. A medical device comprising:

a handle;

an elongate member extending from the handle, the elongate member defining an elongate member lumen;

a biopsy needle extending through the elongate member lumen, the biopsy needle defining a biopsy needle lumen;

an imaging device extending through the biopsy needle lumen, the imaging device being moveable between a proximal end of the biopsy needle and a distal end of the biopsy needle;

an elongate member opening at a distal end of the elongate member;

a biopsy needle deployment feature proximate to the elongate member opening, wherein the biopsy needle deployment feature is:

disposed within the elongate member lumen;

movable, with respect to the elongate member lumen, between a first configuration and a second configuration, and wherein (i) where in the first configuration, the biopsy needle is moveable over the biopsy needle deployment feature and towards the distal end of the elongate member and past the elongate member opening, and (ii) in the second configuration the biopsy needle is moveable through the elongate member opening; and an elongate member recess within the elongate member lumen, the elongate member recess extending from a surface of the elongate member lumen opposite the elongate member opening, the elongate member recess configured to receive a portion of the biopsy needle deployment feature when the biopsy needle deployment feature is in the first configuration where a portion of the biopsy needle deployment feature forms a peak that is planar with the elongate member lumen surface.

2. The medical device of claim 1, wherein in the first configuration, the biopsy needle and the imaging device are moveable past the elongate member opening to the distal end of the elongate member and in the second configuration the biopsy needle and the imaging device are moveable through the elongate member opening.

3. The medical device of claim 2, wherein in the second configuration, the imaging device is retractable within the biopsy needle when the biopsy needle extends through the elongate member opening.

4. The medical device of claim 1, further comprising:

an illumination feature disposed within the biopsy needle lumen and around the imaging device; and a suction port extending through the biopsy needle and around the imaging device.

5. The medical device of claim 1, further comprising an actuator mechanism movable within the elongate member lumen and coupled with the biopsy needle deployment feature, wherein the actuator mechanism is moveable within the elongate member lumen to place the biopsy needle deployment feature in the first configuration and the actuator mechanism is retractable within the elongate member lumen to place the biopsy needle deployment feature in the second configuration.

6. The medical device of claim 1, further comprising:

an ultrasonic sensor disposed distal to the elongate member opening; and electromagnetic elements proximate the ultrasonic sensor.

7. The medical device of claim 6, wherein the biopsy needle and the imaging device are moveable underneath the ultrasonic sensor to the distal end of the elongate member.

8. The medical device of claim 1, further comprising landmarks at an interior of the biopsy needle and viewable by the imaging device when the imaging device is moved within the biopsy needle.

9. The medical device of claim 1, wherein the biopsy needle deployment feature is formed of a bendable alloy where in the second configuration, the biopsy needle deployment feature forms a peak that extends into the elongate member opening.

10. The medical device of claim 1, wherein the imaging device is a complementary metal-oxide semiconductor (CMOS) sensor that faces a distal end of the biopsy needle.

11. The medical device of claim 1, further comprising an inflator cuff disposed at an outer surface of the elongate member proximate to the elongate member.

12. A medical device comprising:

a handle;

an elongate member extending from the handle, the elongate member defining an elongate member lumen;

a biopsy needle extending through the elongate member lumen, the biopsy needle defining a biopsy needle lumen;

an imaging device extending through the biopsy needle lumen, the imaging device moveable between a proximal end of the biopsy needle and a distal end of the biopsy needle;

an elongate member opening at a distal end of the elongate member;

a biopsy needle deployment feature proximate to the elongate member opening, wherein the biopsy needle deployment feature is:

disposed within the elongate member lumen;

movable, with respect to the elongate member lumen, between a first configuration and a second configuration, and wherein (i) where in the first configuration, the biopsy needle is extendable over the biopsy needle deployment feature and towards the distal end of the elongate member and past the elongate member opening, and (ii) in the second configuration the biopsy needle is moveable through the elongate member opening;

an actuator mechanism movable within the elongate member lumen and coupled with the biopsy needle deployment feature, wherein the actuator mechanism is extendable within the elongate member lumen to place the biopsy needle deployment feature in the first configuration and the actuator mechanism is retractable within the elongate member lumen to place the biopsy needle deployment feature in the second configuration.

13. The medical device of claim 12, wherein:

in the first configuration, the biopsy needle and the imaging device are moveable past the elongate member opening to the distal end of the elongate member and in the second configuration the biopsy needle and the imaging device are moveable through the elongate member opening; and in the second configuration, the imaging device is retractable within the biopsy needle when the biopsy needle extends through the elongate member opening.

14. The medical device of claim 12, further comprising: an ultrasonic sensor disposed distal to the elongate member opening; and electromagnetic elements proximate the ultrasonic sensor, wherein the biopsy needle and the imaging device are moveable underneath the ultrasonic sensor to the distal end of the elongate member.

15. The medical device of claim 12, further comprising an elongate member recess within the elongate member lumen, the elongate member recess extending from a surface of the elongate member lumen opposite the elongate member opening, the elongate member recess configured to receive a portion of the biopsy needle deployment feature when the biopsy needle deployment feature is in the first configuration where a portion of the biopsy needle deployment feature forms a peak that is planar with the elongate member lumen surface.

16. The medical device of claim 12, wherein the biopsy needle deployment feature is formed of a bendable alloy where in the second configuration, the biopsy needle deployment feature forms a peak that extends into the elongate member opening.

17. A medical device comprising:

a handle;

an elongate member extending from the handle, the elongate member defining an elongate member lumen;

a biopsy needle extending through the elongate member lumen, the biopsy needle defining a biopsy needle lumen;

an imaging device extending through the biopsy needle lumen, the imaging device extendable between a proximal end of the biopsy needle and a distal end of the biopsy needle;

an elongate member opening at a distal end of the elongate member;

a biopsy needle deployment feature proximate to the elongate member opening, wherein the biopsy needle deployment feature is:

disposed within the elongate member lumen;

movable, with respect to the elongate member lumen, between a first configuration and a second configuration, and wherein (i) where in the first configuration, the biopsy needle is moveable over the biopsy needle deployment feature and towards the distal end of the elongate member and past the elongate member opening, and (i) in the second configuration the biopsy needle is moveable through the elongate member opening;

landmarks at an interior of the biopsy needle and viewable by the imaging device when the imaging device is retracted within the biopsy needle; and an elongate member recess within the elongate member lumen, the elongate member recess extending from a surface of the elongate member lumen opposite the elongate member opening, the elongate member recess configured to receive a portion of the biopsy needle deployment feature when the biopsy needle deployment feature is in the first configuration where a portion of the biopsy needle deployment feature forms a peak that is planar with the elongate member lumen surface.

18. The medical device of claim 17, further comprising an actuator mechanism movable within the elongate member lumen and coupled with the biopsy needle deployment feature, wherein the actuator mechanism is moveable within the elongate member lumen to place the biopsy needle deployment feature in the first configuration and the actuator mechanism is retractable within the elongate member lumen to place the biopsy needle deployment feature in the second configuration.

19. The medical device of claim 17, further comprising: an ultrasonic sensor disposed distal to the elongate member opening; and electromagnetic elements proximate the ultrasonic sensor, wherein the biopsy needle and the imaging device are moveable underneath the ultrasonic sensor to the distal end of the elongate member, wherein the landmark is used to determine an amount of a sample within the biopsy needle.

* * * * *